United States Patent [19]
Nilsson et al.

[11] Patent Number: 5,921,922
[45] Date of Patent: Jul. 13, 1999

[54] MEASURING OF BLOODGASES

[75] Inventors: Gert Nilsson; Folke Sjöberg, both of Linköping, Sweden

[73] Assignee: Forskarpatent I Linkoping AB, Linkoping, Sweden

[21] Appl. No.: 08/732,217

[22] PCT Filed: Apr. 24, 1995

[86] PCT No.: PCT/SE95/00446

§ 371 Date: Dec. 18, 1996

§ 102(e) Date: Dec. 18, 1996

[87] PCT Pub. No.: WO95/29401

PCT Pub. Date: Nov. 2, 1995

[30]     Foreign Application Priority Data

Apr. 25, 1994   [SE]   Sweden ................................ 9401457

[51] Int. Cl.$^6$ .......................... A61B 5/14; G01N 27/30
[52] U.S. Cl. ...................... 600/353; 600/361; 600/364; 204/403; 436/68
[58] Field of Search .................... 128/632, 635; 204/403, 412; 436/68; 600/345, 348, 350, 353, 355, 361, 364

[56]     References Cited

U.S. PATENT DOCUMENTS 3,923,626  12/1975  Niedrach et al. ..................... 128/635
4,685,465   8/1987  Klitgaard et al. .

FOREIGN PATENT DOCUMENTS 247 941   12/1987  European Pat. Off. .
299 778    1/1989  European Pat. Off. .
351 516    1/1990  European Pat. Off. .
2731930    1/1978  Germany .

*Primary Examiner*—Cary E. O'Connor
*Assistant Examiner*—Eric F. Winakur
*Attorney, Agent, or Firm*—Pillsbury Madison & Sutro LLP

[57]     ABSTRACT

A method and an equipment for determining components, particularly pH, $pO_2$ and $pCO_2$ in blood. In order to facilitate the determination of blood gases, one sensor is used for measurement of more than one component. The components are measured at the same measuring point, using an electrode based on antimony. The electrode potential is measured both with and without a known voltage applied over the electrode.

10 Claims, 5 Drawing Sheets

MEASURING OF BLOODGASES

This application is the national phase of international application PCT/SE95/0046 filed Apr. 24, 1995 which designated the U.S.

BACKGROUND OF THE INVENTION

This invention is related to a method and an equipment for the measuring and determining in an electric way by means of a common electrode at least two components, for instance pH and $pO_2$, which are parts of the electrode potential of the electrode. In particular, the invention concerns measuring of pH and $pO_2$ with one and the same antimony electrode.

The measuring of bloodgases constitutes one of the cornerstones within the medical diagnostics. The oxygen value $pO_2$ describes how well the blood is saturated by oxygen in the lungs and how good the saturation by oxygen is in relation to the oxygen needs of the tissues, and the blood becomes acidified, that is the pH-value is reduced when the requirements are greater than the available oxygen. Another central parameter in the analysis of bloodgases is the carbon dioxide level, $pCO_2$, which is a measurement of how well the sugar decomposing products are ventilated from the lung.

Since the middle of the 19the century, it has been a goal in the art to find good systems for the measuring of pH, $PO_2$ and $pCO_2$ in blood and tissue.

The standard method for measuring pH has since long time being with glass based electrodes. The drawback of these have been that they are brittle and suffer from drift, which contributes to the impossibility of using them for continuous measuring in blood or tissue or for instance, control of patients.

The standard method for measuring oxygen levels in medical appliances has been by means of a Clark electrode. This has a complex structure including the enclosing of the electrode in a number of membranes and corresponding electrolytic solutions to provide a stable measuring system. The complexity of the construction and the drift of the measuring device has, however resulted in that it is not possible to use, for a clark electrode continuous measurements for supervising or control proposes. The tendency of thrombosis continuous around the electrode has further contributed to the difficulties.

Also, for the measuring of carbon dioxide continuously in the bloodstream or tissue of patients a good method and equipment is missing today. The traditional equipment for this is based on a pH-electrode which is placed inside a membrane that is previous to carbon dioxide. The solution inside the membrane is a buffer that, through the addition of the carbon dioxide from the measured environment, will become more acid when the carbon dioxide is dissolved in the fluid to make carbonic acid. The acidification inside the membrane is then proportional to the carbon dioxide levels outside the membrane, and can be measured by means of a conventional pH-electrode.

From the Swedish patent document 409 372 a metal electrode for the measuring of pH, etc. in liquids is previously known. This electrode consist of a sensor of metal enclosed in a holder; the metal is monocrystaline with only one crystal plane exposed to the testing liquid. With such an electrode made of antimony, pH measuring with high resolution (0.02 pH-units) is made possible. This electrode type has the same good characteristic for pH measuring as glass-based pH electrodes and have several practical advantages in comparison to the glass electrode since the electrode type is less vulnerable, easy to sterilise and not harmful to biological tissue.

A remaining problem with antimony-based electrodes is however, the oxygen dependency. This has been investigated in a number of studies, where among other things, it has been shown that the oxygen-dependent part of the electrode voltage is stable, thereby enabling simultaneous oxygen measuring, provided that the pH component can be identified and subtracted. In the described case (Sjöberg, P. Skeletal muscle surface pH and $PO_2$. Linköping University Medical Dissertations No 325, 1990. Linköping), where the electrode has been used for tissue measuring, this has been carried out by for a short time cutting off the flow of blood to the tissue. This results in the oxygen pressure for a short time becoming 0 and it is thereby possible to identify pH part of the signal. By then subtracting the pH part of the signal, the oxygen levels before the cutoff can be calculated. The drawback with this method is that the cutoff may influence the cutogg environment of the measuring. And, some tissues cannot endure the cutoff method, for instance the central nervous system. It should therefore be of a great value to be able to separate the two components of the electrode voltage in an electrical manner.

SUMMARY OF THE INVENTION

One purpose of this invention is to separate the two signal parts at an antimony-based or other metal electrode in a reliable and simple way, so that values for $pO_2$ and pH can be obtained from one and the same sensor. A second object is to obtain values of $pO_2$ and $pCO_2$ from one and the same sensor in a similar manner. A further object is to obtain these pairs of measured values from the same measuring point. These and other objects are obtained with the invention in accordance with the appended patent claims.

BRIEF DESCRIPTION OF THE DRAWINGS

The invention is now to be described more in detail with reference to the appended drawings, in which.

DETAILED DESCRIPTION

Figure 1:
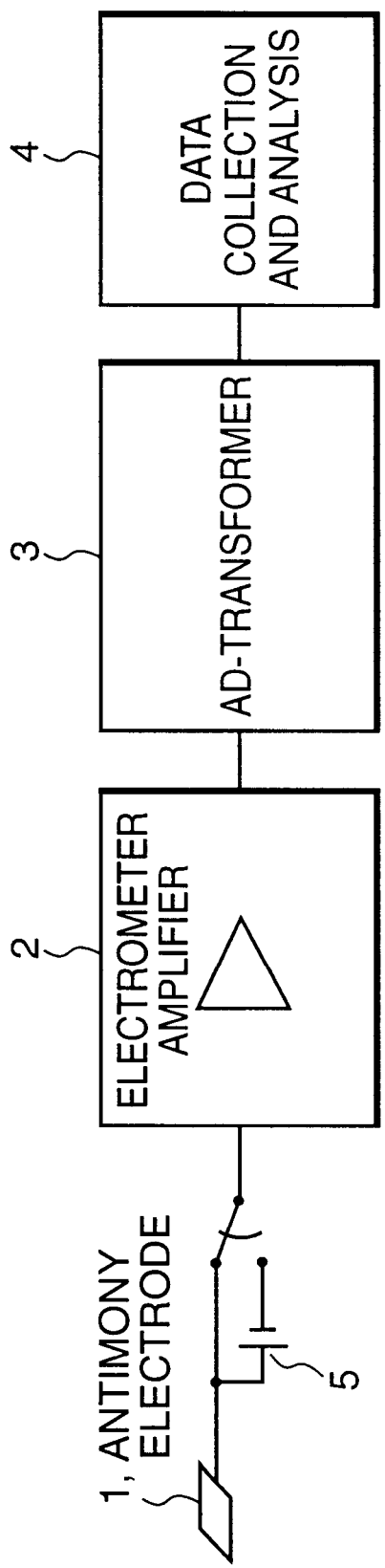
FIG. 1 shows schematically a measuring device for the execution of a measuring method in accordance with the invention.

The measurement in accordance with equipment FIG. 1 is constituted by an antimony electrode 1 coupled to an electrometer amplifier 2 with a high impedance, an AD-transformer 3 and a device for data collection and analysis 4 that can be constituted by a personal computer. The electrometer amplifier enables potentiometric voltage measuring with a high resolution (0.01 mV), and polarographic measurement, comprising subjecting -the electrode to a voltage and measuring of the current flowing through the electrode. The measurement resolution is in this connection on the order of one nanoampere. For polarographic measurement, the voltage may be varied between +1 V and +1 V. This is done by means of the connectable voltage source 5, at the connection of which the electrometer amplifier 2 is reset for current measuring.

Figure 2:
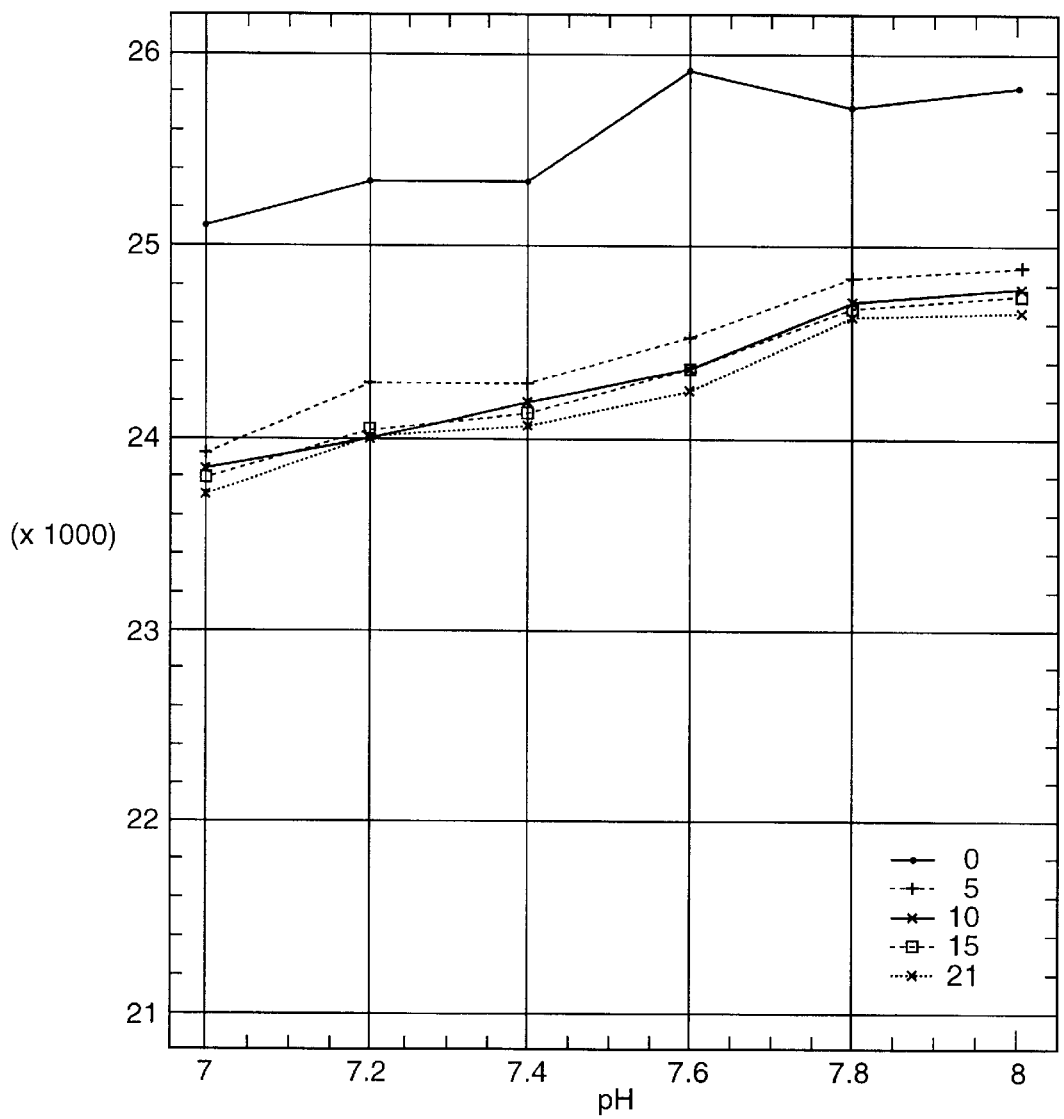
FIG. 2 shows the voltage as a function of the pH value from an antimony electrode for different oxygen concentrations.
Figure 3:
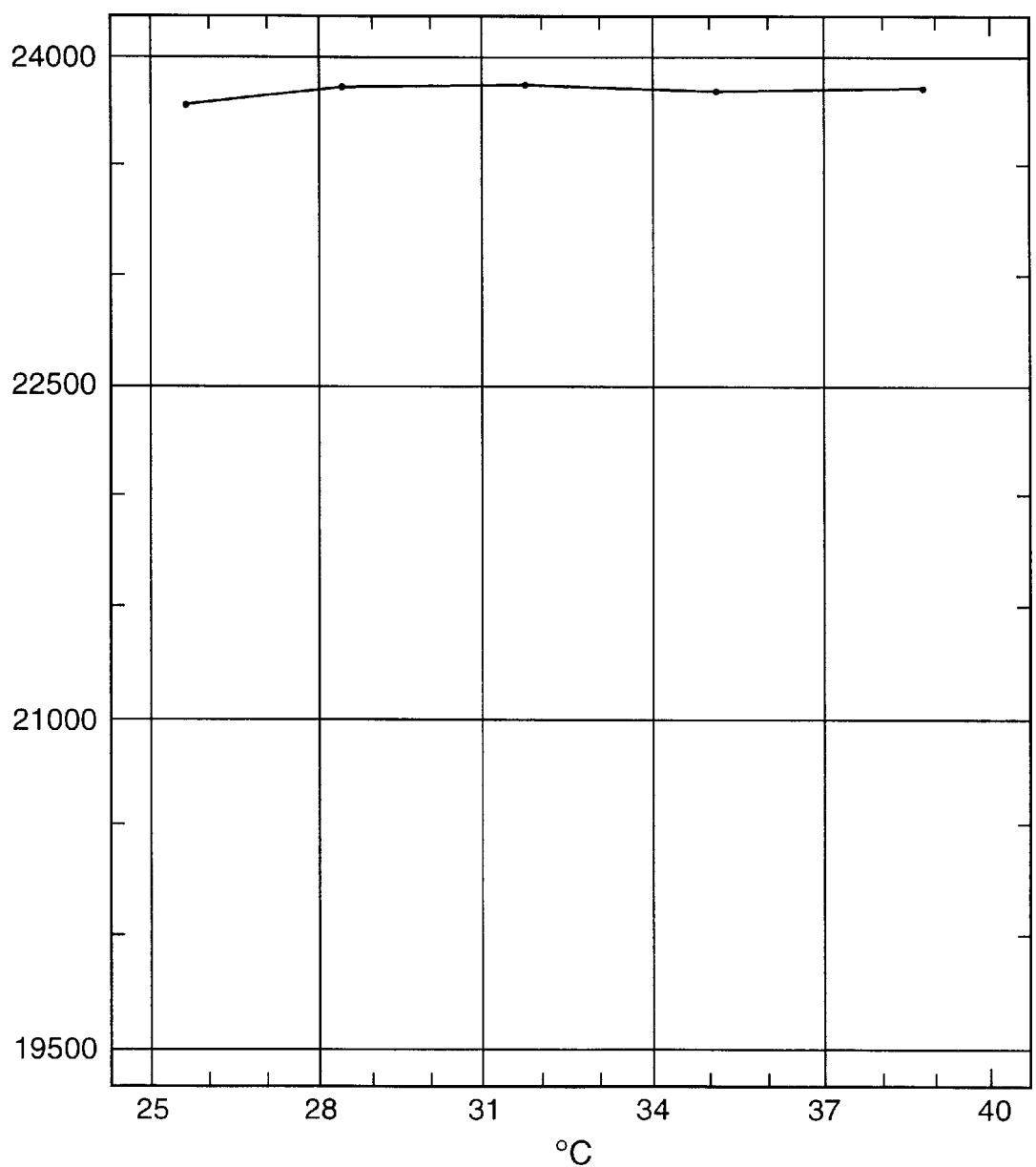
FIG. 3 shows the voltage of an antimony electrode as a function the temperature.
Figure 4:
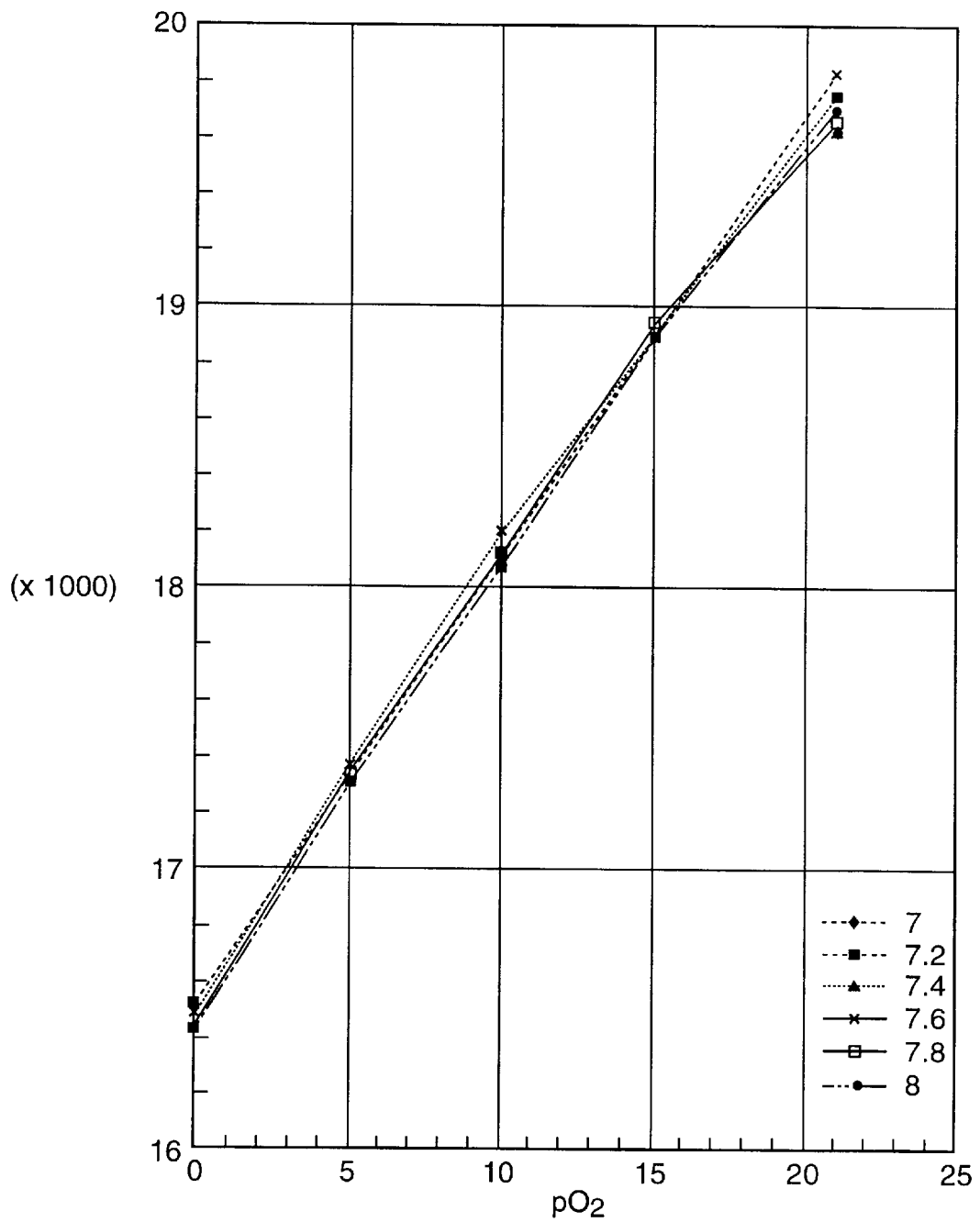
FIG. 4 shows the current as a function of the oxygen pressure for different pH values at a polarographic measurement with an antimony electrode.
Figure 5:
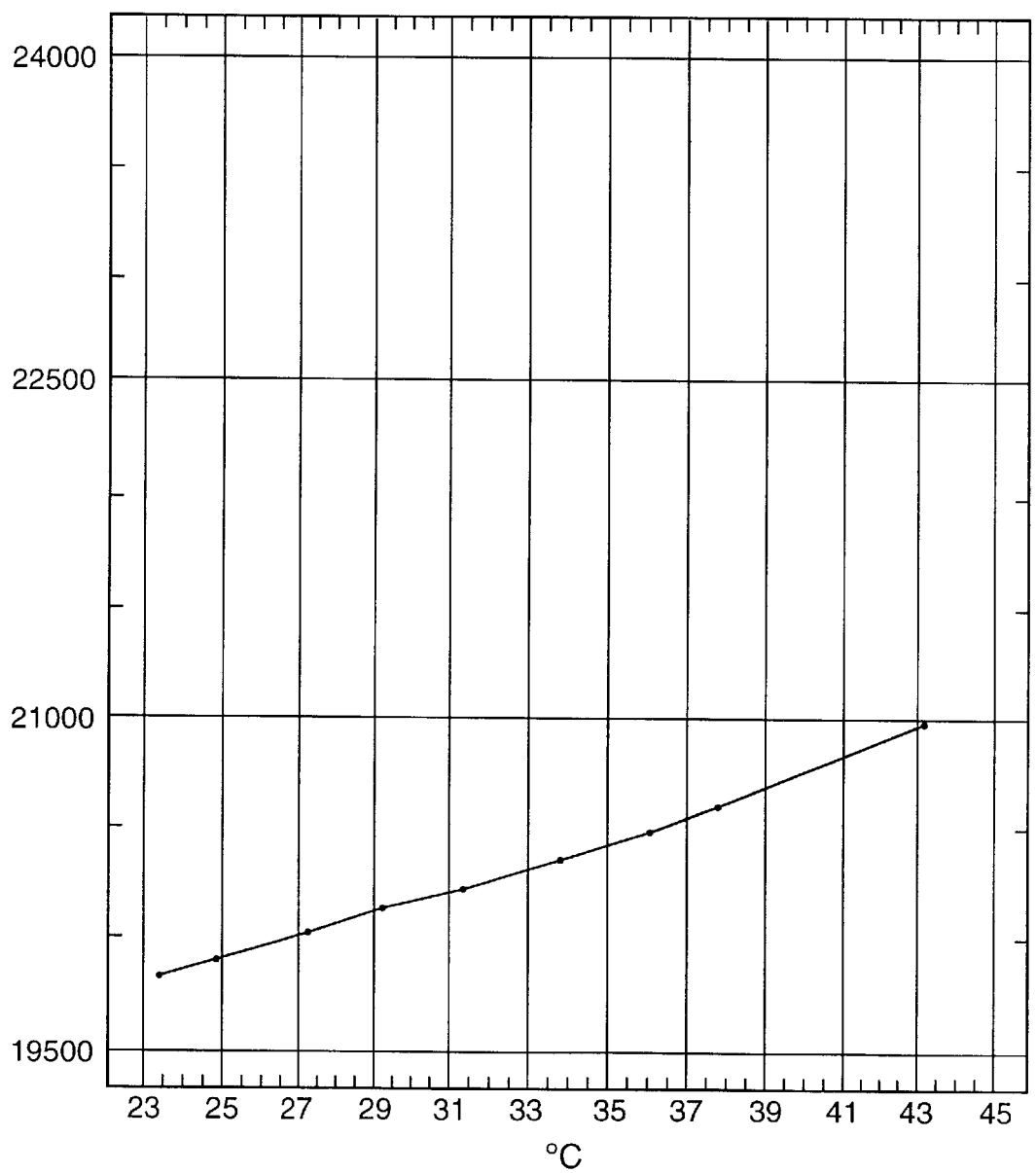
FIG. 5 shows the current as a function of the temperature at polarographic measuring.

For tests carried out according to the invention, a electrode of highly refined monocrystaline a crystalographicly orientated antimony has been used, with a diameter of 1 mm, enclosed in a cylindrically shaped epoxy plastic shroud. The electrode surface is covered with a membrane of polytetrafluoro ethylene and enclosed in a measuring chamber which is placed in a water bath, where the temperature may be monitored with good precision. The electrode may be exposed to different gases through a system of hoses extending to the measuring chamber. For the following described test, that is shown in the diagrams according to FIGS. 2–5, the electrode has been exposed to five different mixtures of gases, AGA special gas containing 0, 5, 10, 15 and 21% of oxygen and different buffers (TRIS) 7.0, 7,2, 7.4, 7.6, 7.8 and 8.0, while the electrode has been set for potentiometric (FIG. 2 and 3) or polarographic (FIG. 4 and 5) measuring. The Y-axes of the diagrams are given with the unit bit, that with known scale factors can be recalculated to a voltage in V respectively a current in A.

During an investigation of the potentiometric measuring properties of the electrode type, results essentially identically to previous investigations of the electrode characteristics of the antimony have been obtained. It is thus from FIG. 2 apparent that the oxygen sensitivity has a non-linear dependency with high sensitivities in the interval 0–10 kPa. It is further from FIG. 3 apparent that the pH sensitivity is high and linear (58 mV/pH-units). It is further apparent from these tests that the temperature dependency is linear and thereby compensatible, and that the response time of the electrode is extremely short, on the order of milliseconds.

When investigating the polarographic properties of the electrode type, that is with a DC voltage applied over the electrode, a study of the current-voltage curves of the electrode, a similar pattern was obtained as the one obtained with the classical Clark electrode. The difference lies in the voltage plateau being around 900 mV, in comparison with 700 mV for platinum. Since the curve has a plateau-like program the antimony is well-suited for oxygen measurements in this set-up for measuring, provided that the voltage is held constantly around 900 mV, see FIG. 4. The antimony electrode does also at this voltage show a high oxygen sensitivity, recalculated to oxygen pressure 0.005 kPa. The sensitivity is constant within the tested area; that is also interesting from a medical point of view (see FIG. 5). This electrode reaction has also turned out to be non pH sensitive, something that strongly simplifies the calculation process. The temperature dependency is, as it is apparent from FIG. 6, linear and compensatable similar to that of Clark electrodes. The response time and the stabilising time at the switching on measuring mode is probably dependent of the close environment of the measuring surface. Times of, at maximum, a few seconds may be acceptable and possible to obtain.

A system for the measuring of $pO_2$ and pH with the same electrode in accordance with what has been described above can be described through the following system of equations, in which U and I are voltage measured at potentiometric measuring and current measured at polarographic measuring, respectively, T is the temperature and A, B, C, D and E are constants:

$U=A(pH)+B(pO_2)+C(T)$ $I=D(pO_2)+E(T)$

By shifting between potentiometric and ampereometric measuring set up with an electrode of a highly refined crystalliographicly orientated antimony, the double sensitivity of the electrode type may in accordance with this invention be separated. The electrode may thereby be used for the measurement of pH as well as $PO_2$, or for the measuring of $PO_2$ as well as $pCO_2$ in the same measuring point. In the latter case, the electrode is surrounded in a way known per se, by a membrane that is permeable to carbon dioxide. The solution inside of the membrane is a buffer that through the addition of the carbon dioxide from the measured environment will have a reduction in pH when the carbon dioxide dissolves in the liquid and makes carbonic acid. The reduction in pH inside the membrane is calculated from the potentiometric, and, the amperometric measured values and since this is proportional to the carbon dioxide level outside the membrane, this can hereby be measured.

The invention is not to be limited by what is described in the described embodiment but only by the wording of the patent claims.

During the polarographic measuring, preferably a voltage is chosen during the measurement in a range, in which the current-voltage curve is as level as possible. This is normally a plateau area that for an antimony electrode is about 900 mV and for an electrode of platinum, 700 mV.

From the above-given equation system, it is obvious that the two measured values obtained at polarographic measuring and at a potentiometric measuring are dependent on pH and oxygen level and the temperature. These dependencies and the corresponding functions can respectively be established by series of tests where pH, oxygen level and temperature are known and a current is measured at polarographic measuring and the voltage at potentiometric measuring. It is then possible to construct correspondency tables for the determination of oxygen level and pH from measured current and voltage. Alternatively, corresponding calculation algorithms may be determined and implemented in a computer equipment.

Since only one very simple electrode of a low-cost material can be used, this may be of a discardable type and very small, with a minimum of inconvenions to the patient. Also, an electrode for accurate measuring of oxygen and carbon dioxide level can be made very small, since it may be made rotationally symmetric and with few and simple components.

The invented method can be used for measurements not only of blood but also for the measurements of other body liquids in the gullet, stomach, etc. The measuring need not necessarily take place inside the body of a patient, but may also take place in a device for dialysis, etc.

We claim:

1. A method for determining two different characteristics of a sample, from one electrode, comprising:

providing an electrode having an active surface constituted by antimony;

while exposing the electrode to a sample which is to be studied, taking current and voltage measurements from said electrode, respectively with and without a known voltage applied over said electrode; and correlating the respective measurements with previously obtained sets of information regarding how respective ones of said characteristics equate to measurements of current and voltage, to obtain measured values for said two different characteristics.

2. The method of claim 1, wherein:

said characteristics are $PO_2$ and pH.

3. The method of claim 1, wherein:

said known voltage is 0.9 volts.

4. Equipment for electrically measuring and evaluating at least two characteristics from the electrical potential of an electrode, comprising:

an electrode having an active surface constituted by antimony;

a voltage source;

means for connecting the voltage source to the electrode;

means for sensitively measuring current or voltage;

and means for alternatively coupling the means for sensitively measuring current or voltage to the electrode for alternatively measuring voltage and current.

5. The equipment of claim 4, wherein:

said means for sensitively measuring are arranged for measuring pH and $pO_2$ of a sample to which the electrode is exposed.

6. The equipment of claim 4, further comprising:

a membrane permeable to carbon dioxide, said membrane enclosing the electrode;

a liquid buffer surrounding the electrode, within the membrane, said liquid buffer being capable of dissolving carbon dioxide therein to produce carbonic acid, thereby reducing pH within the membrane, so that said equipment is able to measure carbon dioxide outside the membrane, for enabling calculation of $pCO_2$ and $pO_2$ outside the membrane.

7. The equipment of claim 4, wherein:

said means for sensitively measuring and said means for alternatively coupling are integrated into one physical structure.

8. The equipment of claim 4, further comprising:

an AD-transformer arranged for transforming values obtained from said means for sensitively measuring; and registering and calculating means for storing values obtained from said means for sensitively measuring, and for performing calculations of results from values.

9. A method for measuring pH and oxygen level in liquid blood, comprising:

providing an electrode of monocrystaline antimony, having only one crystal plane exposed to the liquid blood;

performing potentiometric measuring by measuring the voltage over the electrode to obtain a voltage measurement value;

performing polarographic measuring by measuring the current over the electrode to obtain a current measurement value; and calculating pH and oxygen level of said liquid blood from said voltage and current values.

10. The method of claim 9, wherein:

while performing said polarographic measuring, applying a voltage to the electrode that is within a plateau range of a current-voltage curve for the electrode.

* * * * *